United States Patent
Smith et al.

(10) Patent No.: US 9,549,758 B2
(45) Date of Patent: Jan. 24, 2017

(54) SURGICAL ACCESS ASSEMBLY WITH ADAPTER

(75) Inventors: Robert C. Smith, Middletown, CT (US); Anibal Rodrigues, Milford, CT (US)

(73) Assignee: Covidien LP, Mansfield, MA (US)

( * ) Notice: Subject to any disclaimer, the term of this patent is extended or adjusted under 35 U.S.C. 154(b) by 286 days.

(21) Appl. No.: 13/371,639

(22) Filed: Feb. 13, 2012

(65) Prior Publication Data

US 2012/0245428 A1    Sep. 27, 2012

Related U.S. Application Data

(60) Provisional application No. 61/466,562, filed on Mar. 23, 2011.

(51) Int. Cl.
*A61B 1/32* (2006.01)
*A61B 17/34* (2006.01)

(52) U.S. Cl.
CPC ........ *A61B 17/3423* (2013.01); *A61B 17/3431* (2013.01); *A61B 2017/348* (2013.01); *A61B 2017/3419* (2013.01); *A61B 2017/3429* (2013.01); *A61B 2017/3435* (2013.01); *A61B 2017/3466* (2013.01)

(58) Field of Classification Search
CPC ............ A61B 17/0218; A61B 17/3423; A61B 17/3421; A61B 17/3445; A61B 17/32; A61M 13/003
USPC ............. 600/201–249; 604/174, 175, 103.03
See application file for complete search history.

(56) References Cited

U.S. PATENT DOCUMENTS

| | | | |
|---|---|---|---|
| 5,366,478 A | | 11/1994 | Brinkerhoff et al. |
| 5,524,644 A | * | 6/1996 | Crook ........................ 128/888 |
| 5,549,637 A | | 8/1996 | Crainich |
| 5,553,675 A | | 9/1996 | Pitzen et al. |
| 5,564,615 A | | 10/1996 | Bishop et al. |
| 5,609,560 A | | 3/1997 | Ichikawa et al. |
| 5,634,937 A | | 6/1997 | Mollenauer et al. |

(Continued)

FOREIGN PATENT DOCUMENTS

| EP | 0950376 A1 | 10/1999 |
|---|---|---|
| EP | 2229900 A1 | 9/2010 |

(Continued)

OTHER PUBLICATIONS

European Search Report for corresponding EP12160727 date of mailing is Jun. 15, 2012 (8 pgs).

(Continued)

*Primary Examiner* — Eduardo C Robert
*Assistant Examiner* — Michelle C Eckman (57) ABSTRACT

A surgical access assembly is disclosed, including a resiliently compressible access port defining a longitudinal axis and having proximal and distal ends. At least one lumen extends from the proximal end to the distal end of the access port and is substantially parallel to the longitudinal axis. The surgical access assembly includes a resiliently compressible adapter having proximal and distal ends, an opening at the proximal end, and a passage for receipt of the access port. The adapter has a diameter at its distal end different from the diameter of the distal end of the access port. The adapter has at least one opening in its distal end to allow an object to exit the at least one lumen. The surgical access assembly may also include a sleeve positionable through an opening in tissue.

22 Claims, 8 Drawing Sheets

(56) References Cited

U.S. PATENT DOCUMENTS

| | | |
|---|---|---|
| 5,735,791 A | 4/1998 | Alexander, Jr. et al. |
| 6,033,426 A | 3/2000 | Kaji |
| 6,033,428 A | 3/2000 | Sardella |
| 6,077,288 A | 6/2000 | Shimomura et al. |
| 6,165,169 A | 12/2000 | Panescu et al. |
| 6,254,534 B1 | 7/2001 | Butler et al. |
| 6,382,211 B1 | 5/2002 | Crook |
| 6,440,063 B1 | 8/2002 | Beane et al. |
| 6,450,983 B1 | 9/2002 | Rambo |
| 6,558,371 B2 | 5/2003 | Dorn |
| 6,582,364 B2 | 6/2003 | Butler et al. |
| 6,743,240 B2 | 6/2004 | Smith et al. |
| 6,958,037 B2 | 10/2005 | Ewers et al. |
| 6,972,026 B1* | 12/2005 | Caldwell et al. ............. 606/213 |
| 7,033,319 B2 | 4/2006 | Pulford et al. |
| 7,163,510 B2 | 1/2007 | Kahle et al. |
| 7,195,590 B2* | 3/2007 | Butler et al. ................. 600/207 |
| 7,445,597 B2* | 11/2008 | Butler et al. ................. 600/208 |
| 7,575,144 B2 | 8/2009 | Ortiz et al. |
| 7,588,175 B2 | 9/2009 | Timm et al. |
| 7,704,207 B2 | 4/2010 | Albrecht et al. |
| 7,721,931 B2 | 5/2010 | Shelton, IV et al. |
| 7,727,146 B2 | 6/2010 | Albrecht et al. |
| 7,738,971 B2 | 6/2010 | Swayze et al. |
| 7,803,151 B2 | 9/2010 | Whitman |
| 7,922,061 B2 | 4/2011 | Shelton, IV et al. |
| 8,035,487 B2 | 10/2011 | Malackowski |
| 8,231,527 B2* | 7/2012 | Beckman et al. ............. 600/208 |
| 8,282,546 B2* | 10/2012 | Shelton et al. ............... 600/206 |
| 8,323,184 B2* | 12/2012 | Spiegal et al. ............... 600/206 |
| 8,348,855 B2 | 1/2013 | Hillely et al. |
| 8,758,391 B2 | 6/2014 | Swayze et al. |
| 8,806,973 B2 | 8/2014 | Ross et al. |
| 8,875,972 B2 | 11/2014 | Weisenburgh, II et al. |
| 8,893,946 B2 | 11/2014 | Boudreaux et al. |
| 8,899,462 B2 | 12/2014 | Kostrzewski et al. |
| 8,939,344 B2 | 1/2015 | Olson et al. |
| 8,960,519 B2 | 2/2015 | Whitman et al. |
| 8,961,396 B2 | 2/2015 | Azarbarzin et al. |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,064,653 B2 | 6/2015 | Prest et al. |
| 9,113,875 B2 | 8/2015 | Viola et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 2001/0037053 A1 | 11/2001 | Bonadio et al. |
| 2002/0049454 A1 | 4/2002 | Whitman et al. |
| 2002/0165541 A1 | 11/2002 | Whitman |
| 2003/0014076 A1* | 1/2003 | Mollenauer et al. ......... 606/213 |
| 2003/0165794 A1 | 9/2003 | Matoba |
| 2004/0002632 A1* | 1/2004 | D'Arrigo et al. ............. 600/210 |
| 2005/0288558 A1* | 12/2005 | Ewers et al. ................. 600/206 |
| 2006/0142740 A1 | 6/2006 | Sherman et al. |
| 2006/0161050 A1 | 7/2006 | Butler et al. |
| 2006/0247678 A1 | 11/2006 | Weisenburgh, II et al. |
| 2007/0023476 A1 | 2/2007 | Whitman et al. |
| 2008/0021359 A1 | 1/2008 | Beckman et al. |
| 2008/0021362 A1* | 1/2008 | Fihe et al. ...................... 602/75 |
| 2008/0167736 A1 | 7/2008 | Swayze et al. |
| 2008/0237296 A1 | 10/2008 | Boudreaux et al. |
| 2008/0308603 A1 | 12/2008 | Shelton et al. |
| 2009/0090763 A1 | 4/2009 | Zemlok et al. |
| 2009/0093752 A1* | 4/2009 | Richard et al. ................. 604/24 |
| 2009/0326330 A1* | 12/2009 | Bonadio et al. .............. 600/201 |
| 2010/0041957 A1* | 2/2010 | Urano et al. ................. 600/236 |
| 2010/0094094 A1* | 4/2010 | DeSantis et al. ............. 600/217 |
| 2010/0130825 A1* | 5/2010 | Piskun .......................... 600/204 |
| 2010/0130826 A1* | 5/2010 | Piskun .......................... 600/204 |
| 2010/0137691 A1* | 6/2010 | Piskun .......................... 600/204 |
| 2010/0193568 A1 | 8/2010 | Scheib et al. |
| 2010/0211053 A1 | 8/2010 | Ross et al. |
| 2010/0240960 A1* | 9/2010 | Richard ........................ 600/208 |
| 2010/0249516 A1* | 9/2010 | Shelton et al. ............... 600/203 |
| 2010/0249520 A1* | 9/2010 | Shelton et al. ............... 600/206 |
| 2010/0249521 A1* | 9/2010 | Shelton et al. ............... 600/206 |
| 2010/0249523 A1* | 9/2010 | Spiegal et al. ............... 600/206 |
| 2010/0249524 A1* | 9/2010 | Ransden et al. .............. 600/207 |
| 2010/0249527 A1* | 9/2010 | Brustad et al. ............... 600/208 |
| 2010/0261970 A1* | 10/2010 | Shelton et al. ............... 600/203 |
| 2010/0280326 A1* | 11/2010 | Hess et al. .................... 600/206 |
| 2010/0280327 A1* | 11/2010 | Nobis et al. .................. 600/210 |
| 2010/0286483 A1* | 11/2010 | Bettuchi et al. .............. 600/207 |
| 2010/0286484 A1* | 11/2010 | Stellon et al. ................ 600/208 |
| 2010/0298646 A1* | 11/2010 | Stellon et al. ................ 600/208 |
| 2010/0312061 A1* | 12/2010 | Hess et al. .................... 600/201 |
| 2010/0312064 A1* | 12/2010 | Weisenburgh et al. ....... 600/206 |
| 2010/0312066 A1* | 12/2010 | Cropper et al. ............... 600/207 |
| 2011/0009703 A1* | 1/2011 | Smith ........................... 600/203 |
| 2011/0009704 A1* | 1/2011 | Marczyk et al. ............. 600/207 |
| 2011/0021877 A1* | 1/2011 | Fortier et al. ................. 600/206 |
| 2011/0021879 A1* | 1/2011 | Hart et al. .................... 600/207 |
| 2011/0028891 A1* | 2/2011 | Okoniewski .................... 604/26 |
| 2011/0034778 A1* | 2/2011 | Kleyman ...................... 600/208 |
| 2011/0054257 A1* | 3/2011 | Stopek ......................... 600/206 |
| 2011/0054258 A1* | 3/2011 | O'Keefe et al. .............. 600/206 |
| 2011/0066001 A1* | 3/2011 | Shelton et al. ............... 600/208 |
| 2011/0071508 A1 | 3/2011 | Duval et al. |
| 2011/0082341 A1* | 4/2011 | Kleyman et al. ............. 600/206 |
| 2011/0082343 A1* | 4/2011 | Okoniewski .................. 600/208 |
| 2011/0082346 A1* | 4/2011 | Stopek ......................... 600/215 |
| 2011/0112374 A1* | 5/2011 | Brustad et al. ............... 600/208 |
| 2011/0118552 A1* | 5/2011 | Fischvogt .................... 600/206 |
| 2011/0118553 A1* | 5/2011 | Stopek ......................... 600/245 |
| 2011/0124967 A1* | 5/2011 | Morgan et al. ............... 600/204 |
| 2011/0124968 A1* | 5/2011 | Kleyman ...................... 600/206 |
| 2011/0124970 A1* | 5/2011 | Kleyman ...................... 600/208 |
| 2011/0144444 A1* | 6/2011 | Sakai et al. ................... 600/206 |
| 2011/0155786 A1 | 6/2011 | Shelton, IV |
| 2011/0166423 A1* | 7/2011 | Farascioni et al. ........... 600/208 |
| 2011/0172648 A1 | 7/2011 | Jeong |
| 2011/0174099 A1 | 7/2011 | Ross et al. |
| 2011/0196302 A1* | 8/2011 | Gildersleeve et al. ........ 604/151 |
| 2011/0201893 A1* | 8/2011 | O'Prey et al. ................ 600/208 |
| 2011/0251463 A1* | 10/2011 | Kleyman ...................... 600/205 |
| 2011/0251464 A1* | 10/2011 | Kleyman ...................... 600/206 |
| 2011/0251465 A1* | 10/2011 | Kleyman ...................... 600/208 |
| 2011/0251466 A1* | 10/2011 | Kleyman et al. ............. 600/208 |
| 2011/0276057 A1 | 11/2011 | Conlon et al. |
| 2011/0295074 A1* | 12/2011 | Stefanchik et al. ........... 600/201 |
| 2011/0295077 A1* | 12/2011 | Stefanchik et al. ........... 600/210 |
| 2012/0074199 A1 | 3/2012 | Olson et al. |
| 2012/0083660 A1* | 4/2012 | Okoniewski .................. 600/207 |
| 2012/0083661 A1* | 4/2012 | Rockrohr ..................... 600/208 |
| 2012/0089131 A1 | 4/2012 | Zemlok et al. |
| 2012/0104071 A1 | 5/2012 | Bryant |
| 2012/0116368 A1 | 5/2012 | Viola |
| 2012/0130177 A1* | 5/2012 | Davis ........................... 600/201 |
| 2012/0130179 A1* | 5/2012 | Rockrohr ..................... 600/205 |
| 2012/0130181 A1* | 5/2012 | Davis ........................... 600/206 |
| 2012/0130182 A1* | 5/2012 | Rodrigues et al. ........... 600/206 |
| 2012/0130183 A1* | 5/2012 | Barnes ......................... 600/206 |
| 2012/0130184 A1* | 5/2012 | Richard ........................ 600/208 |
| 2012/0130185 A1* | 5/2012 | Pribanic ....................... 600/208 |
| 2012/0130186 A1* | 5/2012 | Stopek et al. ................ 600/208 |
| 2012/0130187 A1* | 5/2012 | Okoniewski .................. 600/208 |
| 2012/0130188 A1* | 5/2012 | Okoniewski .................. 600/208 |
| 2012/0130189 A1* | 5/2012 | Kleyman ...................... 600/208 |
| 2012/0130190 A1* | 5/2012 | Kasvikis ....................... 600/208 |
| 2012/0130191 A1* | 5/2012 | Pribanic ....................... 600/208 |
| 2012/0143007 A1* | 6/2012 | Haig et al. .................... 600/206 |
| 2012/0149987 A1* | 6/2012 | Richard et al. ............... 600/205 |
| 2012/0157779 A1* | 6/2012 | Fischvogt .................... 600/207 |
| 2012/0157780 A1* | 6/2012 | Okoniewski et al. ........ 600/207 |
| 2012/0157781 A1* | 6/2012 | Kleyman ............. A61B 17/3423 600/208 |
| 2012/0157782 A1* | 6/2012 | Alfieri .......................... 600/208 |
| 2012/0157784 A1* | 6/2012 | Kleyman et al. ............. 600/208 |
| 2012/0157786 A1* | 6/2012 | Pribanic ....................... 600/208 |
| 2012/0165611 A1* | 6/2012 | Warren et al. ................ 600/204 |
| 2012/0190931 A1* | 7/2012 | Stopek ......................... 600/207 |

(56) References Cited

U.S. PATENT DOCUMENTS

| | | | | |
|---|---|---|---|---|
| 2012/0190932 | A1* | 7/2012 | Okoniewski | 600/207 |
| 2012/0190933 | A1* | 7/2012 | Kleyman | 600/207 |
| 2012/0209077 | A1* | 8/2012 | Racenet | 600/206 |
| 2012/0209078 | A1* | 8/2012 | Pribanic et al. | 600/208 |
| 2012/0238825 | A1* | 9/2012 | Smith | 600/207 |
| 2012/0245423 | A1* | 9/2012 | Rodrigues | 600/205 |
| 2012/0245425 | A1* | 9/2012 | Okoniewski | 600/207 |
| 2012/0245427 | A1* | 9/2012 | Kleyman | 600/208 |
| 2012/0245428 | A1* | 9/2012 | Smith et al. | 600/208 |
| 2012/0245429 | A1* | 9/2012 | Smith | 600/208 |
| 2012/0245430 | A1* | 9/2012 | Kleyman et al. | 600/208 |
| 2012/0253134 | A1* | 10/2012 | Smith | 600/203 |
| 2012/0253136 | A1* | 10/2012 | Rodrigues, Jr. | 600/208 |
| 2012/0283520 | A1* | 11/2012 | Kleyman | 600/208 |
| 2012/0289785 | A1* | 11/2012 | Albrecht et al. | 600/208 |
| 2012/0330285 | A1 | 12/2012 | Hartoumbekis et al. | |
| 2013/0093149 | A1 | 4/2013 | Saur et al. | |
| 2013/0181035 | A1 | 7/2013 | Milliman | |
| 2013/0184704 | A1 | 7/2013 | Beardsley et al. | |
| 2013/0274722 | A1 | 10/2013 | Kostrzewski et al. | |
| 2013/0324978 | A1 | 12/2013 | Nicholas et al. | |
| 2013/0324979 | A1 | 12/2013 | Nicholas et al. | |
| 2013/0334281 | A1 | 12/2013 | Williams | |
| 2014/0207125 | A1 | 7/2014 | Applegate et al. | |
| 2014/0373652 | A1 | 12/2014 | Zergiebel et al. | |
| 2015/0157321 | A1 | 6/2015 | Zergiebel et al. | |
| 2015/0164502 | A1 | 6/2015 | Richard et al. | |
| 2015/0272577 | A1 | 10/2015 | Zemlok et al. | |
| 2015/0297199 | A1 | 10/2015 | Nicholas et al. | |
| 2015/0303996 | A1 | 10/2015 | Calderoni | |
| 2015/0320420 | A1 | 11/2015 | Penna et al. | |
| 2015/0327850 | A1 | 11/2015 | Kostrzewski | |
| 2015/0342601 | A1 | 12/2015 | Williams et al. | |
| 2015/0342603 | A1 | 12/2015 | Zergiebel et al. | |
| 2015/0374366 | A1 | 12/2015 | Zergiebel et al. | |
| 2015/0374370 | A1 | 12/2015 | Zergiebel et al. | |
| 2015/0374371 | A1 | 12/2015 | Richard et al. | |
| 2015/0374372 | A1 | 12/2015 | Zergiebel et al. | |
| 2015/0374449 | A1 | 12/2015 | Chowaniec et al. | |
| 2015/0380187 | A1 | 12/2015 | Zergiebel et al. | |
| 2016/0095585 | A1 | 4/2016 | Zergiebel et al. | |
| 2016/0095596 | A1 | 4/2016 | Scirica et al. | |
| 2016/0106406 | A1 | 4/2016 | Cabrera et al. | |
| 2016/0113648 | A1 | 4/2016 | Zergiebel et al. | |
| 2016/0113649 | A1 | 4/2016 | Zergiebel et al. | |

FOREIGN PATENT DOCUMENTS

| | | |
|---|---|---|
| EP | 2289438 A1 | 3/2011 |
| EP | 2668910 A2 | 12/2013 |
| KR | 20120022521 A | 3/2012 |
| WO | 2006040748 A1 | 4/2006 |
| WO | WO2006/115893 A2 | 11/2006 |
| WO | WO2008/011358 A1 | 1/2008 |

OTHER PUBLICATIONS

Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, mailed Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.

\* cited by examiner

SURGICAL ACCESS ASSEMBLY WITH ADAPTER

CROSS REFERENCE TO RELATED APPLICATION

The present application claims the benefit of and priority to U.S. Provisional Application Ser. No. 61/466,562, filed on Mar. 23, 2011, the entire contents of which are incorporated herein by reference.

BACKGROUND

1. Technical Field

The present disclosure relates to an access assembly for use in minimally invasive surgical procedures, such as endoscopic or laparoscopic-type procedures, and more particularly to an access assembly with a surgical access port with an adapter.

2. Background of Related Art

Today, many surgical procedures are performed through small incisions in the skin, as compared to the larger incisions typically required in traditional procedures, in an effort to reduce both trauma to the patient and recovery time. Generally, such procedures are referred to as endoscopic, unless performed on the patient's abdomen, in which case the procedure is referred to as laparoscopic. Throughout the present disclosure, the term minimally invasive should be understood to encompass both endoscopic and laparoscopic procedures. During a typical minimally invasive procedure, surgical objects, such as surgical access ports (e.g., trocar and/or cannula assemblies), endoscopes, or other instruments, are inserted into the patient's body through the incision in tissue. Prior to the introduction of the surgical object into the patient's body, insufflation gases may be used to enlarge the area surrounding the target surgical site to create a larger, more accessible work area. Accordingly, the maintenance of a substantially fluid-tight seal is desirable so as to minimize the escape of insufflation gases and the deflation or collapse of the enlarged surgical site.

To this end, various access members are used during the course of minimally invasive procedures and are widely known in the art. A continuing need exists for an access member of a universal size that can be inserted into a variety of tissue incision sites and maintain the conditions of the insufflated surgical site. It is desirable to accommodate a variety of tissue incisions and body surface conditions, and adapt to changing conditions at the surgery site.

SUMMARY

In accordance with various embodiments, the present disclosure is directed toward a surgical access assembly with an access port and an adapter, both of which in various embodiments maybe formed of a resiliently compressible material, e.g., foam, to sealably fit in a surgical site.

An access port defines a longitudinal axis and has proximal and distal ends. The ends of the surgical access port are defined by a pair of flanges. Disposed through the access port along a path substantially parallel to the longitudinal axis is at least one lumen.

An adapter receives the surgical access port, the adapter having proximal and distal ends. The adapter has a diameter at its distal end that is different from the surgical access port. The adapter has a flange on at least its distal end, and contains an internal recess near the distal end to receive the flange at the distal end of the access port. The adapter has at least one exit aperture in its distal end to allow objects to exit the at least one lumen in the access port.

In another embodiment, the adapter also has a flange on its proximal end, with an internal recess disposed near the proximal end for receiving the flange at the proximal end of the access port. Thus, the surgical access port is disposed entirely within the adapter.

In a further embodiment, the adapter has no flanges at its ends, and is disposed on the outer surface of the access port between the flanges at the ends of the access port. Also present is a tissue engaging member having proximal end and a distal end that engage a body surface and an internal tissue wall. The proximal end and distal end of the tissue engaging member are defined by rings that may contain a rigid or resilient element for rolling portions of the tissue engaging member so as to shorten its length.

In another embodiment of the surgical access assembly, the proximal end of the adapter is rolled away from the access port and down toward a body surface. Thus, the axial length of the adapter may be changed. The rolled end of the adapter may also act as a flange, giving an operator control over the size of the flange.

In still another embodiment of the surgical access assembly, the adapter contains a gap in its outer circumference, and the gap is biased to a closed position when an access port is inserted into the adapter.

Also disclosed is a method of placing a surgical access assembly in a surgical site. The operator will select a surgical access port, and insert the surgical access port into an adapter. A tissue engaging member may also be present at the surgical site, and can be inserted before or in conjunction with the access port and adapter. Surgical instruments may be inserted through the lumens in the surgical access port to an internal body cavity below, and a minimally invasive procedure may be performed. Surgical instruments may then be removed from the at least one lumen, and the surgical access assembly can be removed from the surgical site.

The various aspects of this disclosure will be more readily understood from the following detailed description when read in conjunction with the appended drawings.

DETAILED DESCRIPTION OF EMBODIMENTS

The present disclosure will now describe in detail embodiments of a surgical access assembly with reference to the drawings in which like reference numerals designate identical or substantially similar parts in each view. Throughout the description, the term "proximal" will refer to the portion of the assembly closest to the operator, whereas the term "distal" will refer to the portion of the assembly farthest from the operator. Although discussed in terms of an incision for a minimally invasive procedure, the presently disclosed surgical access assembly may be used in any naturally occurring orifice (e.g. mouth, anus, or vagina).

Figure 1:
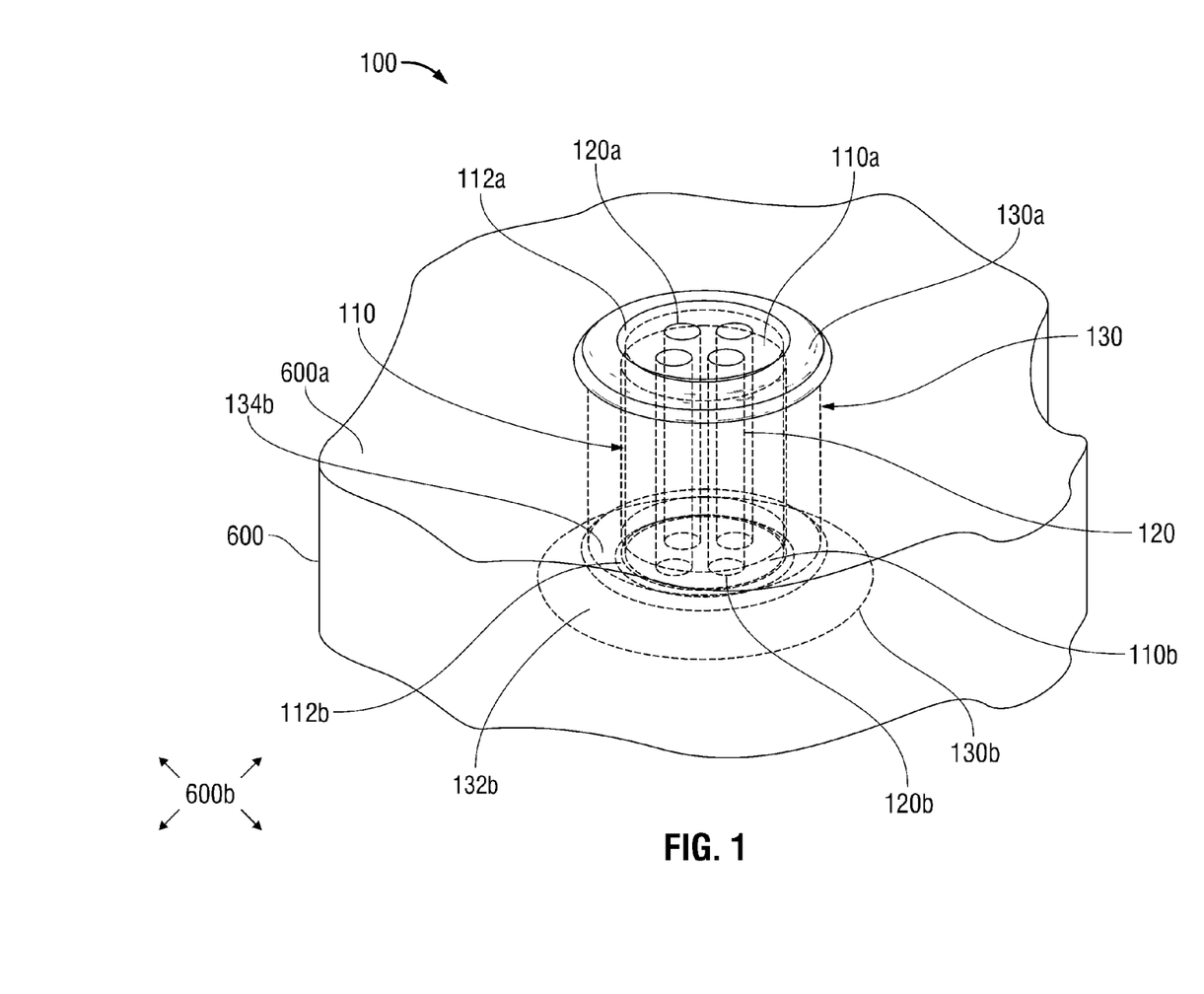
FIG. 1 is a side perspective view of a surgical access assembly with a surgical access port having an adapter and disposed in a layer of tissue.
Figure 2:
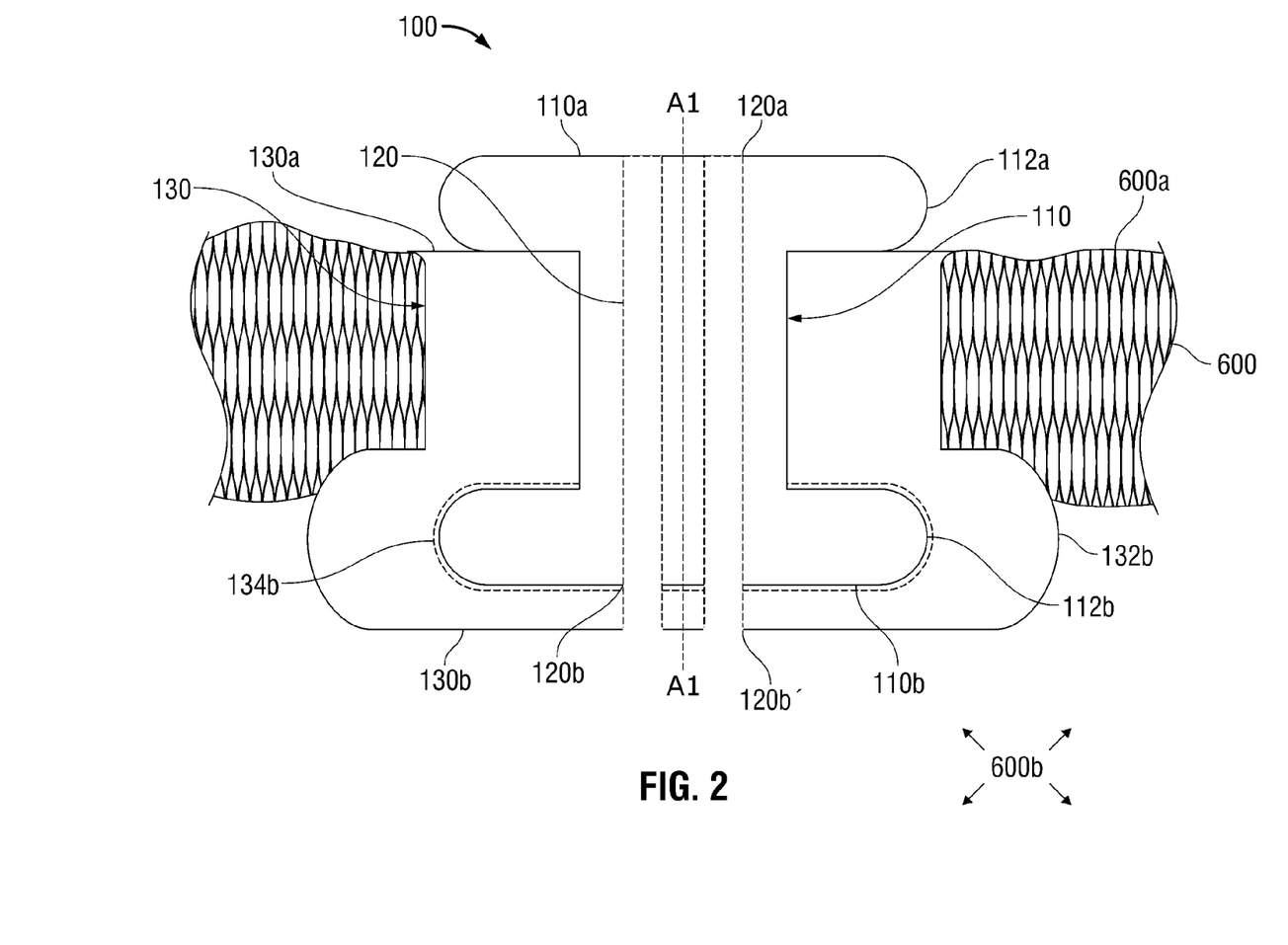
FIG. 2 is a side profile view of the surgical access assembly of FIG. 1, disposed in a layer of tissue and showing lumens in phantom view extending the length of an access port and through an adapter.

Referring initially to FIG. 1, a surgical access assembly 100 is shown. The surgical access assembly 100 includes an access port 110 having a generally hourglass shape, a proximal end 110a and a distal end 110b, and defines a longitudinal axis A1 (FIG. 2). The proximal end 110a and the distal end 110b of the access port 110 are substantially perpendicular to the longitudinal axis A1. A flange 112a defines the proximal end 110a of the access port 110 and a flange 112b defines the distal end 110b of the surgical access port 110. The flanges 112a, 112b may serve to anchor the surgical access assembly 100 into a layer of tissue 600 or to another object. Access port 110 may be formed of a compressible element suitable for contact with internal body surfaces, such as foam.

Extending through the access port 110 along the longitudinal axis A1 is at least one lumen 120, and in embodiments, multiple lumens 120. The lumens 120 have entrance apertures 120a and exit apertures 120b and are disposed substantially parallel to the longitudinal axis A1. Lumens 120 provide a path for objects such as surgical instruments to be inserted through the surgical access assembly 100. Lumens 120 may also provide a path for insufflation fluids to be introduced to an internal body cavity 600b below surgical access assembly 100. An access port of the type generally described above is disclosed in U.S. Patent Application Publication Nos. 2009/0093752 A1 and 2010/0240960 A1, the entire disclosures of which are incorporated by reference herein.

Disposed on an outer surface of the access port 110 is an adapter 130. Adapter 130 has a proximal end 130a and a distal end 130b, and a passage therethrough for the receipt of access port 110. A flange 132b may be present at the distal end 130b of adapter 130. In other embodiments, no flange may be present on adapter 130. A flange 132b at a distal end 130b of adapter 130 may define an internal recess 134b that receives flange 112b at the distal end 110b of access port 110. The engagement of the flange 112b at the distal end 110b of the access port 110 with the internal recess 134b near the distal end 130b of the adapter 130 may serve to anchor the access port 110 to the adapter 130.

Adapter 130 has an inner diameter sized to accommodate a range of access ports. The outer diameter of adapter 130 may be varied so as to sealably engage a layer of tissue 600 of different sizes and configurations. A substantially fluid-tight seal is formed between the inner diameter of adapter 130 and the outer diameter of access port 110. The substantially fluid-tight seal minimizes the escape of insufflation gases from an internal body cavity 600 below surgical access assembly 100.

Adapter 130 and access port 110 may be formed as one single unit, or may be separable, with the access port 110 inserted into adapter 130 before or during use. Access port 110 may also be removed from adapter 130 and replaced with another access member or another object. The outer surface of access port 110 and the inner surface of adapter 130 may frictionally engage upon insertion, or may be provided with a lubricous surface treatment so as to ease insertion.

Turning now to FIG. 2, a side profile view of the surgical access assembly 100 of FIG. 1 is shown disposed in a layer of tissue 600. The access port 110 is seen anchored into adapter 130 by the engagement of the flange 112b at the distal end 110b of the access port 110 with the recess 134b at the distal end 130b of the adapter 130. The engagement of the flange 132b at the distal end 130b of the adapter 130 with the layer of tissue 600 serves to anchor the surgical access assembly 100 into the layer of tissue 600. Flange 132b at the distal end 130b of the adapter 130 will have at least one exit aperture 120b' for objects to exit the surgical access assembly 100.

Figure 3:
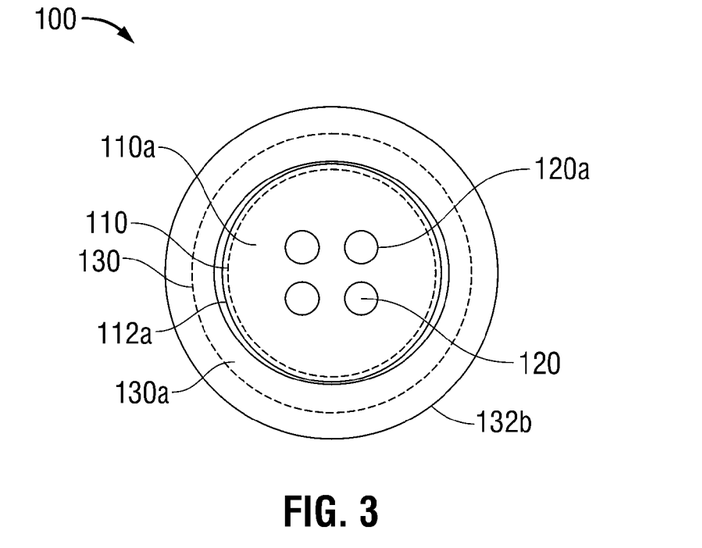
FIG. 3 is a top plan view of the surgical access assembly of FIG. 1, showing the relative placement of the lumens, access port, and adapter.

Referring to FIG. 3, a top plan view of the surgical access assembly 100 of FIG. 1 is shown. The relative positioning of the body of access port 110, lumens 120, flange 112a at the proximal end 110b of access port 110 (shown in phantom view), inner and outer diameter of the adapter 130, and flange 132b at the distal end 130b of adapter 130 can be seen. The lumens 120 and an exit aperture 120b' (FIG. 4) in the distal end 130b of the adapter 130 provide an unobstructed path to the internal body cavity 600b (FIG. 2).

Figure 4:
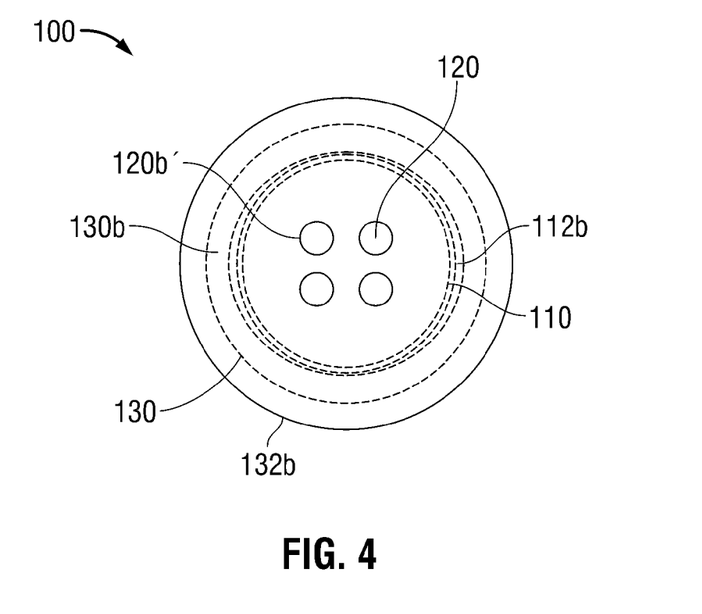
FIG. 4 is a bottom plan view of the surgical access assembly of FIG. 1, showing the relative placement of the lumens, access port, and adapter.

Similarly referring to FIG. 4, a bottom plan view of the surgical access port of FIG. 1 is shown. In this view, the flange 132b at the distal end 130b of the adapter 130 is shown in the foreground in standard view, and exit apertures 120b' for the lumens 120 can also be seen, allowing objects to pass through the surgical access assembly 100 and into internal body cavity 600b (FIG. 2).

Figure 5:
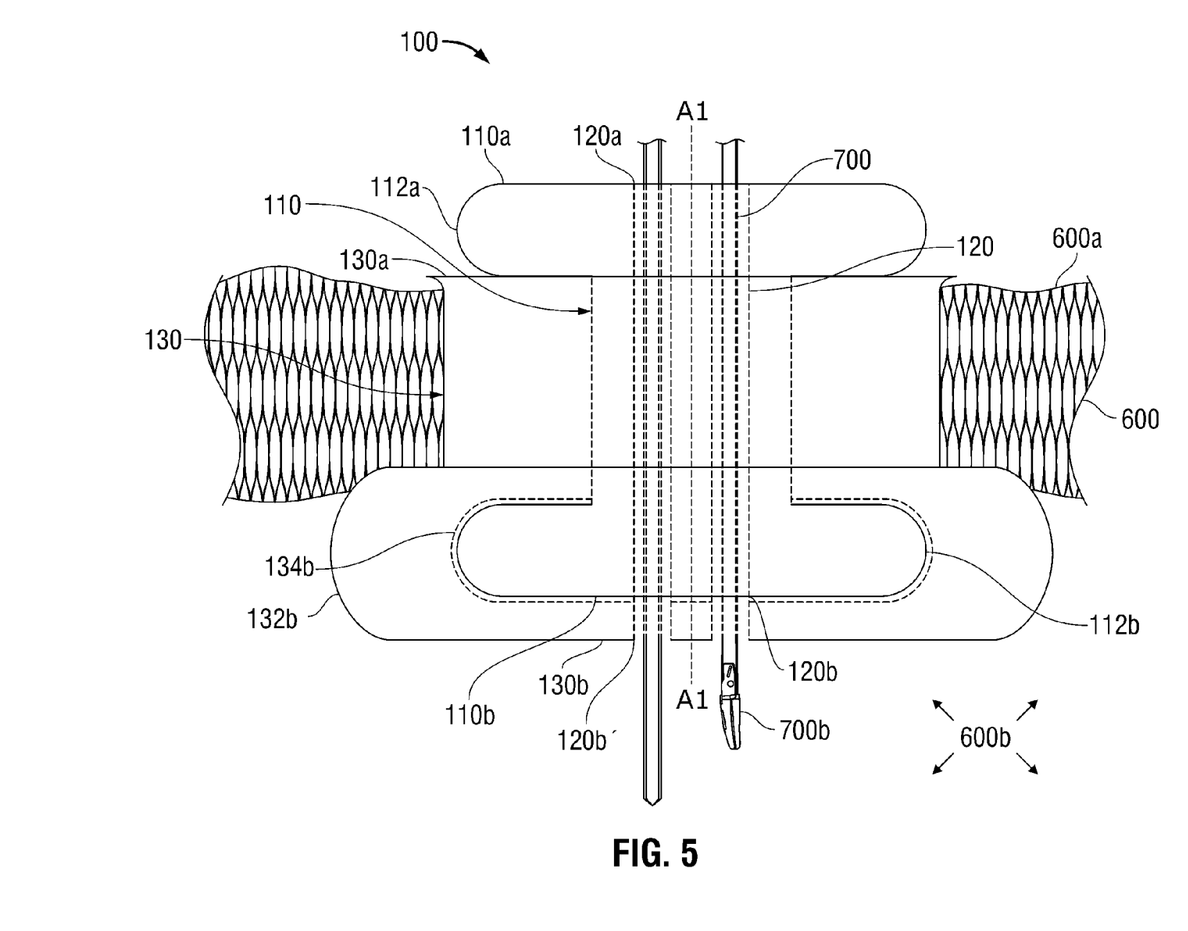
FIG. 5 is a side profile view of the surgical access assembly of FIG. 1, disposed in a layer of tissue with surgical instruments inserted through the lumens.

Turning now to FIG. 5, the surgical access assembly 100 is shown disposed in a layer of tissue 600 and having a pair of surgical instruments 700 inserted through the lumens 120. End effectors 700b of surgical instruments 700 are shown disposed in internal body cavity 600b. Thus, an operator may engage surgical instruments 700 at a point proximal of surgical access assembly 100, and manipulate end effectors 700b to perform desired tasks within internal body cavity 600b.

In use, the operator of the surgical access assembly 100 will insert access port 110 into adapter 130, and dispose the surgical access assembly 100 in a layer of tissue 600. Alternatively, access port 110 may be pre-assembled with adapter 130. Surgical instruments 700 can then be inserted into surgical access port 110 and minimally invasive procedures can be performed. While disposed in a layer of tissue 600, access port 110 may be removed from adapter 130 and replaced with another access member. When a minimally invasive procedure is completed, surgical instruments 700 can be removed from surgical access assembly 100 and the surgical access assembly 100 can then be removed from the layer of tissue 600.

Figure 6:
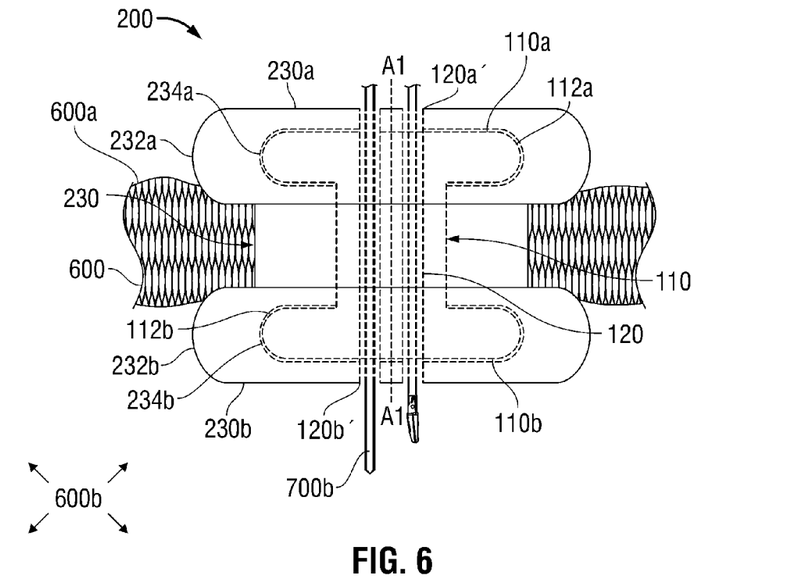
FIG. 6 is a side profile view of an embodiment of a surgical access assembly with an adapter, where the adapter extends proximally above an access port, with surgical instruments inserted therethrough.

Referring to FIG. 6, a side profile view of a surgical access assembly 200 is shown disposed in a layer of tissue 600. Surgical access assembly 200 includes an access port 110 as discussed above with respect to surgical access assembly 100.

Surgical access assembly 200 also contains adapter 230 having a proximal end 230a and a distal end 230b. Adapter 230 is sized to sealably engage access port 110 to minimize the escape of insufflation gases from the internal body cavity 600b below surgical access assembly 200. Adapter 230 includes a flange 232a at the proximal end 230, and a flange 232b at the distal end 230b. An internal recess 234a is present at the proximal end 230a of the adapter 230, and an internal recess 234b is present at the distal end 230b of the adapter 230. Internal recesses 234a, 234b engage flanges 112a, 112b at the proximal end 110a and distal end 110b of access port 110, respectively. Thus, access port 110 is anchored to adapter 230 as it is disposed entirely within adapter 230. Adapter 230 has lumen entrance apertures 120a' and lumen exit apertures 120b' to allow objects to pass through surgical access assembly 200 unobstructed.

Accordingly, surgical instruments 700 are shown inserted through surgical access assembly 200 and into internal body cavity 600b. End effectors 700b of surgical instruments 700 can be manipulated from a point proximal of surgical access assembly 200 to perform desired tasks on an internal body cavity 600b.

Figure 7:
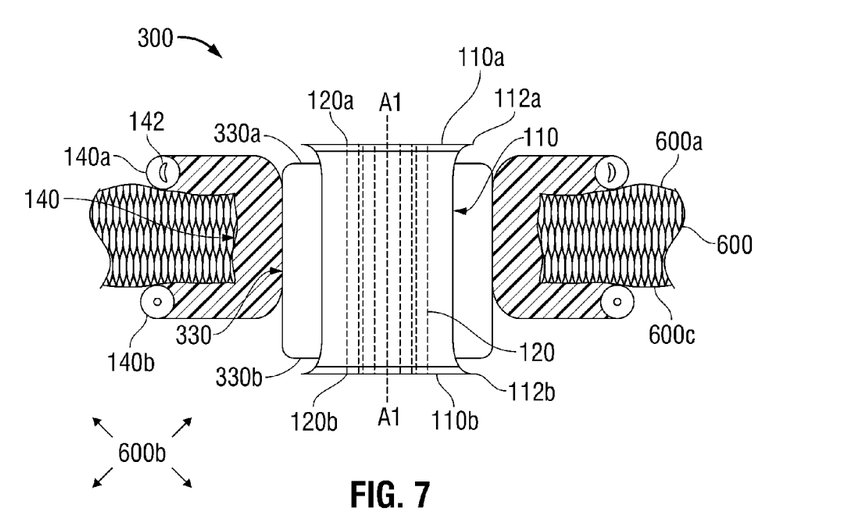
FIG. 7 is a side profile view of an embodiment of a surgical access assembly with an alternate embodiment of an adapter, inserted into a layer of tissue having a tissue engaging member.

Turning now to FIG. 7, a side profile view of a surgical access assembly 300 is shown disposed in a layer of tissue 600. Surgical access assembly 300 includes an access port 110 as discussed above with respect to previous embodiments.

Surgical access assembly 300 also includes an adapter 330. Adapter 330 has a proximal end 330a and a distal end 330b and includes a passage therethrough for receiving access port 110. The inner diameter of adapter sealably engages access port 110 to minimize the escape of insufflation gases from an internal body cavity 600b. The outer diameter of adapter 330 may vary to accommodate a variety of incision sites and tissue layer geometries.

Adapter 330 may extend beyond proximal end 110a or distal end 110b of access port 110 and may include flanges at its proximal end 330a and distal end 330b as in adapters 130, 230 discussed above, or may have an axial length less than access port 110, as shown. In this instance, the adapter 330 is disposed between the flanges 112a, 112b at the proximal end 110a and distal end 110b of the access port 110.

Also included in surgical access assembly 300 is a tissue engaging member 140 having a proximal end 140a and a distal end 140b. Tissue engaging member 140 is disposed around the perimeter of an incision site in a layer of tissue. Tissue engaging member 140 covers a portion of body surface 600a, extends into tissue layer 600, and onto an internal tissue wall 600c. Distal end 140b of tissue engaging member 140 is defined by a ring that contacts internal tissue wall 600c. The ring at the distal end 140b of tissue engaging member may be formed simply by rolling the edge of tissue engaging member 140, or may contain a rigid or resilient ring-like element over which tissue engaging member 140 is rolled. Proximal end 140a of tissue engaging member 140 is also defined by a ring and contacts body surface 600a.

Proximal end 140a of tissue engaging member 140 generally contains a rigid or resilient arcuate element 142 over which tissue engaging member 140 is rolled. The arcuate or kidney bean shape of the arcuate element 142 inhibits the tissue engaging member from unrolling at the proximal end 140a. Other shapes are contemplated as a rigid or resilient rolling member at the proximal end 140a of the tissue engaging member 140. Thus, an operator may shorten the length of tissue engaging member 140 between the proximal end 140a and distal end 140b. Rolling the proximal end 140a of tissue engaging member 140 also exerts force on a layer of tissue 600 such that it may retract tissue.

Tissue engaging member 140 engages the outer surface of adapter 330, and protects tissue layer 600 from damage caused by frictional engagement, shifting during operation, or other harmful forces caused during minimally invasive procedures. Tissue engaging member 140 is separate from access port 110 and adapter 330, and may be inserted into a tissue incision site prior to, or in conjunction with, the introduction of access port 110 and adapter 330. Tissue engaging member 140 is formed of a material suitable for contact with internal body surfaces. Further, the surface of tissue engaging member 140 that is in contact with adapter 330 may be designed to provide an enhanced frictional engagement to secure adapter 330 and access port 110 in place, or may be lubricous so as to ease insertion of the adapter 330 and access port 110 into a layer of tissue 600.

In use, the operator of the surgical access assembly 300 will place tissue engaging member 140 in a layer of tissue 600 such that it protects the tissue walls from damage. The proximal edge 140a of tissue engaging member 140 may then be rolled to adjust the length of tissue engaging member 140 or to retract a tissue wall 600. The operator of the surgical access assembly 300 will then insert access port 110 into adapter 330, and insert them in a layer of tissue 600 such that the outer surface of the adapter 330 engages the tissue engaging member 140. Tissue engaging member 140 and adapter 330 are sized to create a substantially fluid tight seal, and further to secure access port 110 and adapter 330 into a layer of tissue 600. Alternatively, access port 110 may be pre-assembled with adapter 330. Tissue engaging member 140 may also be inserted in conjunction with access port 110 and adapter 330. Minimally invasive procedures can then be performed through the surgical access assembly 300 as described above with respect to surgical access assembly 100.

Figure 8:
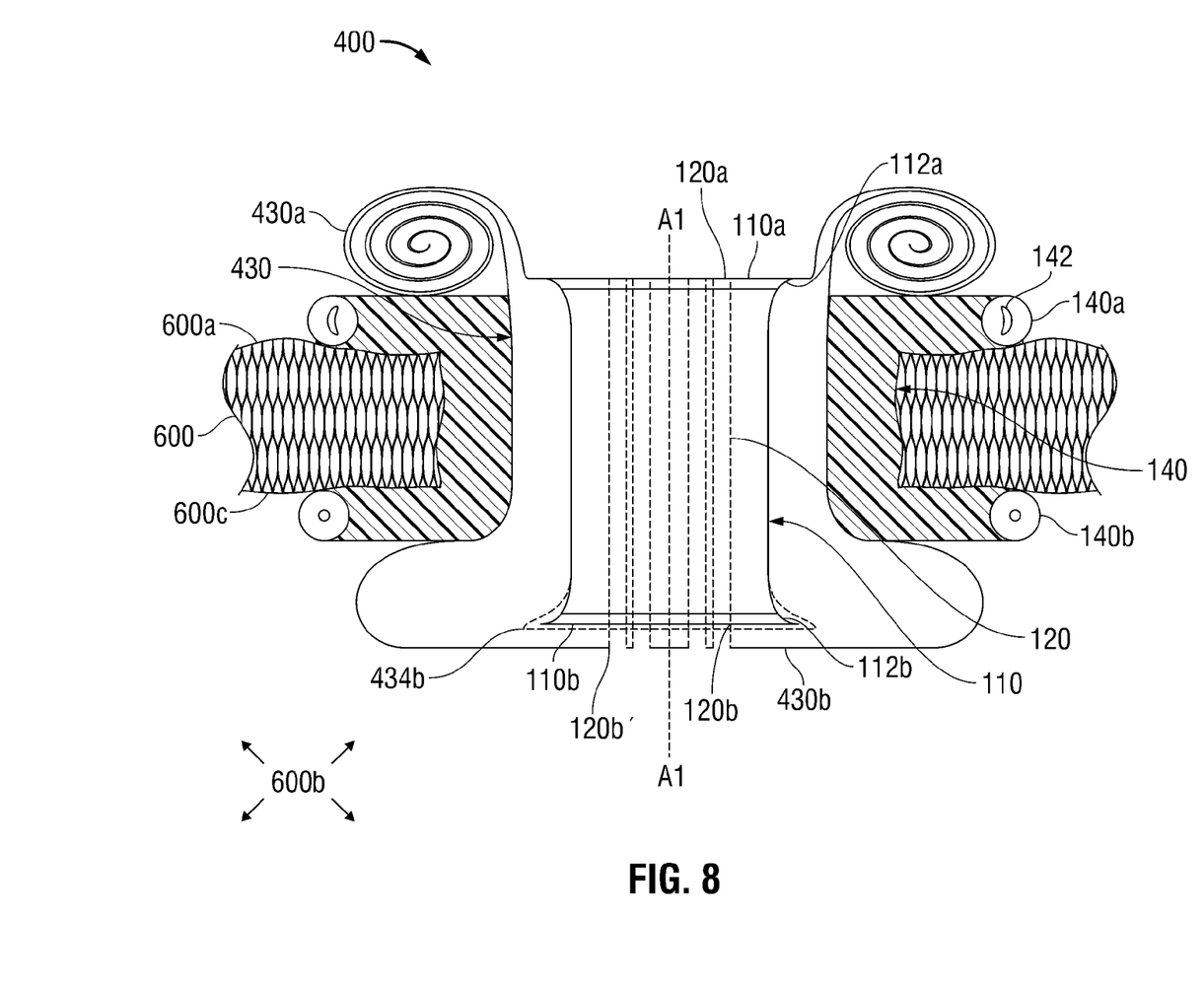
FIG. 8 is an embodiment of a surgical access assembly with an access port and an adapter shown in side profile view, disposed in a layer of tissue having a tissue engaging member, with a proximal end of the adapter rolled down toward a body surface.

Turning to FIG. 8, a surgical access assembly 400 is shown. Surgical access assembly 400 includes an access port 110 and tissue engaging member 140 as discussed above with respect to previous embodiments.

Surgical access assembly 400 includes an adapter 430 that has a proximal end 430a, a distal end 430b, and a passage therethrough for the receipt of access port 110. Adapter 430 sealably engages access port 110 so as to minimize the escape of insufflation gases from the internal body cavity 600b below surgical access assembly 400. As in previous embodiments, distal end 430b of adapter 430 includes an internal recess 434b that engages a flange 112b at the distal end 110b of access port 110. Access port 110 is thus securely anchored in adapter 430.

At a proximal end 430a of adapter 430, the edges of adapter 430 are curled away from the access port 110, and are rolled toward a body surface 600a. Thus, proximal end 430a of adapter 430 is defined by the rolled edge of adapter 430. This may serve to act as a flange as in previous embodiments to anchor surgical access assembly 400 to the layer of tissue 600. The extent to which the edge at the proximal end 430a of adapter 430 is rolled necessarily shortens the length of adapter 430 that is disposed around the body of access port 110. Thus, the operator of the surgical access assembly 400 has the control to change the axial length of the adapter 430.

In use, the operator of the surgical access assembly 400 will insert the tissue engaging member 140 into a layer of tissue 600. The proximal edge 140a of tissue engaging member 140 may then be rolled to adjust the length of tissue engaging member 140 or to retract a tissue wall 600. The operator will then insert the access port 110 into adapter 430. Proximal end 430a of adapter 430 will extend proximally above the access port 110. The operator of the surgical access assembly 400 will curl the proximal end 430a of the adapter 430 away from the access port 110 and roll it toward a body surface 600a to a desired degree. Alternatively, the distal end 430a of the adapter 430 may be rolled after insertion into the tissue engaging member 140 and the layer of tissue 600. Insertion of the access port 110 and the adapter 430 into the tissue engaging member 140 proceeds as described above with respect to surgical access assembly 300. Alternatively, tissue engaging member 140 may be inserted into a tissue layer 600 in conjunction with access port 110 and adapter 430. Minimally invasive procedures can then be performed in a manner described above.

Figure 9:
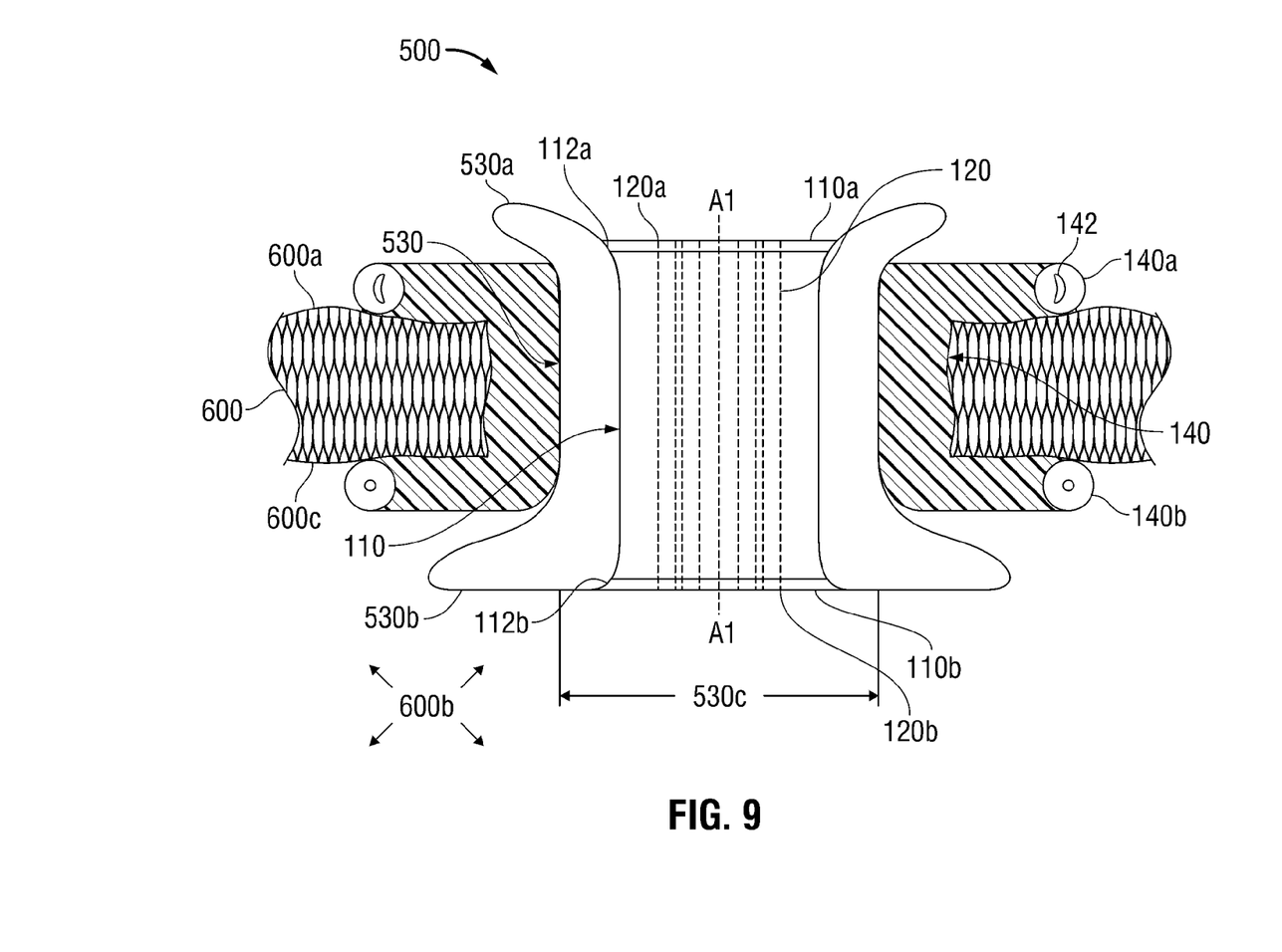
FIG. 9 is an embodiment of a surgical access assembly with an access port and an adapter shown in side profile view, disposed in a layer of tissue having a tissue engaging member, the adapter having a gap in its outer circumference.

Referring to FIG. 9, a surgical access assembly 500 is shown disposed in a layer of tissue 600. Surgical access assembly 500 includes an access port 110 and a tissue engaging member 140 having a configuration substantially similar to access port 110 and tissue engaging member 140 discussed above with respect to previous embodiments.

Surgical access assembly 500 includes an adapter 530 having a proximal end 530a and a distal end 530b, and having a passage therethrough for the receipt of access port 110. Adapter has a gap 530c in its circumference. Adapter 530, upon expansion due to stresses from an object inserted therethrough, biases gap 530c toward a closed position. Thus, when access port 110 is inserted into adapter 530, adapter 530 biases the gap 530c toward a closed position such that adapter 530 is securely engaged around access port 110. The pressed engagement of the access port 110 and adapter 530 in a layer of tissue 600 forms a substantially fluid-tight seal and minimizes the escape of insufflation gases from an internal body cavity 600b below surgical access assembly 500.

In use, an operator of a surgical access assembly 500 inserts the tissue engaging member 140 into a layer of tissue 600. The proximal edge 140a of tissue engaging member 140 may then be rolled to adjust the length of tissue engaging member 140 or to retract a tissue wall 600. The operator will then insert access port 110 into adapter 530. Alternatively, adapter 530 may be wrapped around the outer circumference of access port 110 by widening the gap 530c during placement. With the access port 110 disposed within adapter 530, and adapter 530 expanded in response, adapter 530 tends to bias the gap 530c toward a closed position, thus securing access port 110 in place. Insertion of the surgical access port 110 and adapter 530 into the tissue engaging member 140 and performing minimally invasive procedures proceeds in a manner described above with respect to the previous embodiments. Alternatively, tissue engaging member 140 may be inserted into a layer of tissue 600 in conjunction with surgical access port 110 and adapter 530.

Figure 10:
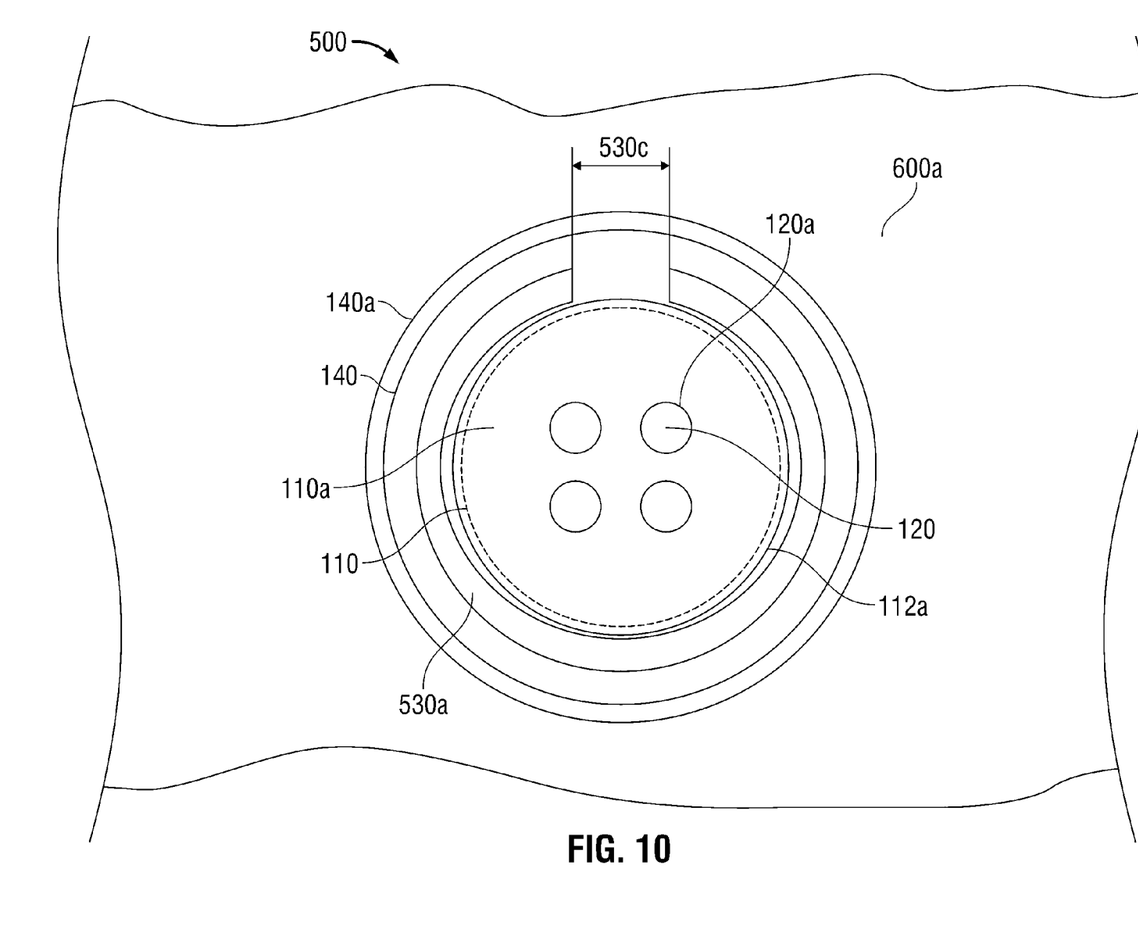
FIG. 10 is a top plan view of the surgical access assembly of FIG. 9, disposed in a layer of tissue and showing the adapter securing an access port in place.

Turning to FIG. 10, a top plan view of surgical access assembly 500 is shown disposed in a layer of tissue 600 (FIG. 9). The relative positioning of the access port 110, adapter 530, and tissue engaging member 140 is shown.

Further, with the access port 110 inserted into adapter 530, the secure engagement of the access port 110 and the adapter 530 is shown as the adapter 530 biases the gap 530c toward a closed position.

It will be understood that various modifications may be made to the embodiments disclosed herein. Therefore, the above description should not be construed as limiting, but merely as exemplifications of embodiments. Those skilled in the art will envision other modifications within the scope and spirit of the present disclosure.

What is claimed is:

1. A surgical access assembly, comprising:
   a tissue engaging member having proximal and distal ends configured to be disposed on a perimeter of an opening in tissue;
   a resiliently compressible access port defining a longitudinal axis and having proximal and distal ends;
   at least one lumen extending from the proximal end to the distal end of the access port, the at least one lumen substantially parallel to the longitudinal axis; and
   a resiliently compressible adapter configured to be received within the tissue engaging member, the adapter having a proximal end and a distal end including a flange defining an interior recess configured to engage the distal end of the access port, the adapter having a passage for the receipt of the access port, the distal end of the adapter having a diameter different from a diameter of the distal end of the access port, and the adapter having at least one opening at the distal end of the adapter configured to receive an object inserted through the at least one lumen of the access port, wherein the at least one opening at the distal end of the adapter and the at least one lumen of the access port are concentrically aligned, wherein a distal-most end of the access port is disposed within the interior recess of the adapter, and the proximal end of the access port engages the proximal end of the adapter.

2. The surgical access assembly of claim 1, wherein the proximal end of the adapter includes a flange.

3. The surgical access assembly of claim 2, wherein the adapter extends proximally above a flange at the proximal end of the access port.

4. The surgical access assembly of claim 1, wherein the access port is configured to transmit insufflation fluid to an internal body cavity.

5. The surgical access assembly of claim 1, wherein the access port and the adapter are coaxial.

6. The surgical access assembly of claim 1, wherein at least one of the proximal or distal ends of the tissue engaging member includes a ring.

7. The surgical access assembly of claim 6, wherein the ring is rigid.

8. The surgical access assembly of claim 1, wherein the proximal end of the adapter is configured to be curled away from the passage and rolled toward a body surface.

9. The surgical access assembly of claim 1, wherein the adapter defines an outer circumference defining a gap therealong, the adapter biasing the gap toward a closed position upon insertion of the access port therein.

10. The surgical access assembly of claim 1, wherein the interior recess of the adapter and the distal end of the access port have complementary cross-sectional configurations.

11. A method of placing a surgical access assembly in an opening in tissue, comprising;
   providing the surgical access assembly including:
      a resiliently compressible access port defining a longitudinal axis and having proximal and distal ends;

at least one lumen extending from the proximal end to the distal end of the access port, the at least one lumen substantially parallel to the longitudinal axis; and a resiliently compressible adapter;

disposing a tissue engaging member having proximal and distal ends on a perimeter of the opening in the tissue;

inserting the access port into the resiliently compressible adapter sized to sealably engage the tissue engaging member disposed in the opening in the tissue, the adapter having a proximal end and a distal end including a flange defining an interior recess configured to engage the distal end of the access port, the adapter including a channel for the receipt of the access port, the distal end of the adapter having a diameter different from a diameter of the distal end of the access port, the adapter having at least one opening at the distal end of the adapter configured to receive an object inserted through the at least one lumen, the at least one opening at the distal end of the adapter and the at least one lumen of the access port being concentrically aligned, a distal-most end of the access port disposed within the interior recess of the adapter, the proximal end of the access port engaging the proximal end of the adapter;

inserting the object through the at least one lumen; and performing a minimally invasive procedure through the access port.

12. The method of claim 11, further comprising removing the object from the at least one lumen.

13. The method of claim 12, further comprising removing the access port from the opening in the tissue.

14. The method of claim 11, further comprising inserting the adapter such that a flange at the proximal end of the adapter abuts the tissue.

15. The method of claim 14, wherein inserting the access port into the adapter includes inserting a flange at the proximal end of the access port into the adapter, such that at least a portion of the adapter is proximal of the flange at the proximal end of the access port.

16. The method of claim 11, further comprising transmitting insufflation fluid to an internal body cavity through the access port.

17. The method of claim 11, further comprising aligning the access port and the adapter coaxially.

18. The method of claim 11, wherein disposing the tissue engaging member on the perimeter of the opening in the tissue includes disposing at least one of the proximal or distal ends of the tissue engaging member having a ring on the perimeter of the opening in the tissue.

19. The method of claim 11, a further comprising rolling the tissue engaging member over a rigid element.

20. The method of claim 19, wherein rolling the tissue engaging member includes rolling the proximal end of the tissue engaging member to adjust a length of the tissue engaging member prior to insertion of the access port.

21. The method of claim 11, further comprising curling the proximal end of the adapter away from the passage, and rolling the proximal end of the adapter toward a body surface.

22. A method of placing a surgical access assembly in an opening in tissue, comprising:

providing the surgical access assembly including:
a resiliently compressible access port defining a longitudinal axis and having proximal and distal ends;
at least one lumen extending from the proximal end to the distal end of the access port, the at least one lumen substantially parallel to the longitudinal axis; and
a resiliently compressible adapter;

inserting the access port into the resiliently compressible adapter sized to sealably engage the opening in the tissue, the adapter having a proximal end and a distal end including a flange defining an interior recess configured to engage the distal end of the access port, the adapter including a channel for the receipt of the access port, the distal end of the adapter having a diameter different from a diameter of the distal end of the access port, the adapter having at least one opening at the distal end of the adapter configured to receive an object inserted through the at least one lumen, the at least one opening at the distal end of the adapter and the at least one lumen of the access port being concentrically aligned, a distal-most end of the access port disposed within the interior recess of the adapter, the proximal end of the access port engaging the proximal end of the adapter;

curling the proximal end of the adapter away from the passage and rolling the proximal end of the adapter toward a body surface;

inserting the object through the at least one lumen; and performing a minimally invasive procedure through the access port.

\* \* \* \* \*